United States Patent [19]

Ohtsubo et al.

[11] Patent Number: 4,590,809
[45] Date of Patent: May 27, 1986

[54] SAMPLER AND AN APPARATUS FOR HYDROGEN DETERMINATION IN MOLTEN METAL

[75] Inventors: Takashi Ohtsubo; Hirahisa Kawase; Syunsuke Goto, all of Kawasakishi, Japan

[73] Assignees: Nippon Steel Corporation; Japan Analyst Corporation, both of Tokyo, Japan

[21] Appl. No.: 748,134

[22] Filed: Jun. 24, 1985

Related U.S. Application Data

[63] Continuation-in-part of Ser. No. 572,531, Jan. 19, 1984, abandoned.

[30] Foreign Application Priority Data

Jan. 22, 1983 [JP] Japan ............................... 58-6748[U]
Jan. 31, 1983 [JP] Japan ................................ 58-12649

[51] Int. Cl.⁴ ............................................ G01N 1/12
[52] U.S. Cl. ............................... 73/863.53; 73/863.52
[58] Field of Search ........... 73/864.52, 864.53, 864.55, 73/864.58

[56] References Cited

U.S. PATENT DOCUMENTS 3,354,723 11/1967 Smith .
3,452,602 7/1969 Hackett ............................ 73/864.55
4,170,139 10/1979 Narita et al. ..................... 73/864.52
4,445,390 5/1984 Atwell .

FOREIGN PATENT DOCUMENTS 887202 11/1971 Canada .............................. 73/864.52

Primary Examiner—Bernard Nozick
Attorney, Agent, or Firm—Wenderoth, Lind & Ponack

[57] ABSTRACT

A sampler for drawing a sample of molten metal for analysis for hydrogen, the sampler has a tubular body of inorganic refractory material having low thermal conductivity and being substantially impermeable to hydrogen, and a readily meltable portion at one end and a hydrogen collection chamber at the other end. An inner tube is completely enclosed within the tubular body and is of a hydrogen permeable material and has a cylindrical space therewithin and defines with the inner surface of the tubular body an annular space between the inner tube and the body. It has apertures communicating the spaces. One of the spaces is open at the end corresponding to the readily meltable portion for receiving molten metal thereinto when the meltable portion is melted when the one end of the sampler is inserted into a bath of molten metal. The end of the one space which is toward the other end of the tubular body from the hydrogen collection chamber is sealed. The other of the spaces is open to the hydrogen collection chamber at the end corresponding to the other end of the tubular body and is closed off from the readily meltable portion.

7 Claims, 10 Drawing Figures

SAMPLER AND AN APPARATUS FOR HYDROGEN DETERMINATION IN MOLTEN METAL

This application is a continuation-in-part of now abandoned application Ser. No. 572,531, filed Jan. 19, 1984.

BACKGROUND OF THE INVENTION

1. Field of the Invention

This invention relates to a device for taking a sample of molten metal for making a determination of the amount of hydrogen therein and an apparatus for the determination of the amount of hydrogen in molten metal.

2. Description of the Prior Art

In order to produce steel or aluminum having good mechanical properties, it is essential to reduce the quantity of hydrogen in the molten metal as far as possible. The determination of the amount of hydrogen in molten metal has conventionally been carried out by taking a sample in a quartz tube directly from the molten metal or with the aid of a spoon, quenching it with water, cutting the solidified sample to an appropriate size immediately or after storing the sample in dry ice or liquid nitrogen, polishing the surface, and analyzing the sample by a method which includes melting in an inert gas, gas chromatographic separation and thermal conductivity determination. A method including vacuum heating and constant volume pressure measurement is also employed for hydrogen determination.

It has, however, been difficult for a number of reasons to conduct an accurate determination of the amount of hydrogen in molten metal. In the first place, the solubility of hydrogen is greatly lowered with the solidification of the molten metal, as shown in FIG. 1 showing by way of example solubility in iron. A large quantity of hydrogen is lost into the ambient air during the solidification of the molten metal, and makes impossible the proper determination of the amount of hydrogen in the molten metal. In the second place, the loss of hydrogen also takes place during the cutting or polishing of the solidified sample, since it is supersaturated with hydrogen at an ambient temperature.

A number of proposals have been made to solve those problems. The first proposal has been to use a vacuum quartz sampling tube containing a stainless steel cylinder having a small wall thickness such that the hydrogen which is released from the molten metal during its solidification is absorbed by the stainless steel in which hydrogen is highly soluble, and then the solidified metal and the stainless steel cylinder are cut together to form a sample (Narita et al., IRON AND STEEL, 65, 1979, 1620). This method has, however, a serious disadvantage. A very small clearance is very likely to be formed between the solidified metal and the stainless steel cylinder, and traps water when the sample is cooled with water. This water is decomposed when the sample is melted for analysis, and the resulting hydrogen causes an error in the determination of the amount of hydrogen in the molten metal. This error is aggravated unless the stainless steel cylinder is completely dehydrogenated previously.

The second proposal relates to a sampler which comprises a hollow body formed by a thin metal wall 1 and caps 3 and a sampling mold 3 contained therein, as shown in Japanese Patent Publication No. 45157/1978. The hollow body is hermetically closed and defines a vacuum chamber 2-1 therein. The cap 2-1 is immersed in molten metal and a sample of the molten metal is drawn into the mold. The sampler is cooled so that hydrogen is released from the molten metal and collected in the vacuum chamber. The greater part of the sampler remote from the cap is placed in a vessel connected to a gas analyzer, and the inlet of the vessel is closed. The wall is pierced to release hydrogen from the vacuum chamber to the analyzer. If the entire sampler is placed in the closed vessel and its wall is pierced with a hole, a part of the hydrogen released from the metal on the suction end of the sampler will also enter the analyzer and give rise to an error in the determination of the amount of hydrogen. This method has the advantage of avoiding the loss of hydrogen which would otherwise occur during the solidification of the sample, or during its cutting or polishing which is no longer necessary. The method has, however, a number of disadvantages, too, as will hereinafter be pointed out:

(1) The sampler is covered by a heat-insulating material which prevents the melting of the thin metal wall 1 when it is immersed in molten metal. The heat-insulating material contains an organic binder. When the sampler is immersed in molten metal, the binder burns and causes the molten metal to boil and draw air thereinto. A part of the heat-insulating material is melted to form slag which increases the quantities of C, H, O, Si and inclusions in the molten metal. These problems make it impossible to use the sampler in a tundish or a mold immediately prior to continuous casting, and make it possible to use the sampler only at an earlier stage.

(2) If the heat-insulating material is removed, it is impossible to avoid the adhesion of molten metal to the outer periphery of the wall and the cap 2-1, even if the sampler is immersed in molten metal for only a short period of time which does not cause any melting of the wall. The metal adhering to the sampler makes it very difficult to achieve a satisfactory seal between the sampler and the vessel and makes any accurate hydrogen determination practically impossible.

(3) A rubber O-ring is usually used to provide a seal between the vessel and the sampler. After a predetermined amount of molten metal has been drawn into the sampler, it is cooled with water so that the O-ring will not be burned. In the case of hydrogen analysis in steel, about 5 to 10% of hydrogen remains in the steel in the mold without being released into the vacuum chamber. Therefore, it is necessary to cut the mold and determine the remaining hydrogen by a hot extraction hydrogen analyzer after determining the amount of hydrogen in the vacuum chamber, and make a total of the two values obtained. This is a serious obstacle to quick analysis.

SUMMARY OF THE INVENTION

It is an object of this invention to provide an improved sampler for the hydrogen analysis of molten metal which overcomes the drawbacks of the prior art as hereinabove pointed out.

It is another object of this invention to provide an improved apparatus for the hydrogen analysis of molten metal.

These objects are attained by the following sampler and apparatus:

(1) A sampler for the hydrogen analysis of molten metal comprising a vacuum tubular body having a wall formed from an inorganic refractory material, and provided at one end thereof with a suction end which is melted upon immersion in molten metal to form an opening for the suction of the molten metal, and a tube connected to the suction end, formed from a hydrogen-permeable material and defining a cavity in which the molten metal drawn thereinto through the suction opening can be solidified in a predetermined shape, the tubular body defining therein a hollow space located contiguous to the tube for collecting the hydrogen released from the molten metal in the tube during its solidification.

(2) An apparatus for the hydrogen analysis of molten metal comprising a sampler which comprises a vacuum tubular body having a wall formed from an inorganic refractory material, and provided at one end thereof with a suction end which is melted upon immersion in molten metal to form an opening for the suction of the molten metal, and a tube connected to the suction end, formed from a hydrogen-permeable material and defining a cavity in which the molten metal drawn thereinto through the suction opening can be solidified in a predetermined shape, the tubular body defining therein a hollow space located contiguous to the tube for collecting the hydrogen released from the molten metal in the tube during its solidification, a hermetically closed vessel for holding the sampler containing the molten metal, means for breaking the sampler in the vessel, and gas analyzer means for determining the quantity of the hydrogen released from the sampler into the vessel when the sampler is broken.

BRIEF DESCRIPTION OF THE DRAWINGS

FIG. 4b is a sectional view taken along the line 4b—4b of FIG. 4a;

FIG. 4c is a sectional view taken along the line 4c—4c of FIG. 4a;

FIG. 5b is a sectional view taken along the line 5a—5a of FIG. 5a;

FIG. 5c is a sectional view taken along the line 5c—5c of FIG. 5a;

DETAILED DESCRIPTION OF THE INVENTION

Figure 4A:
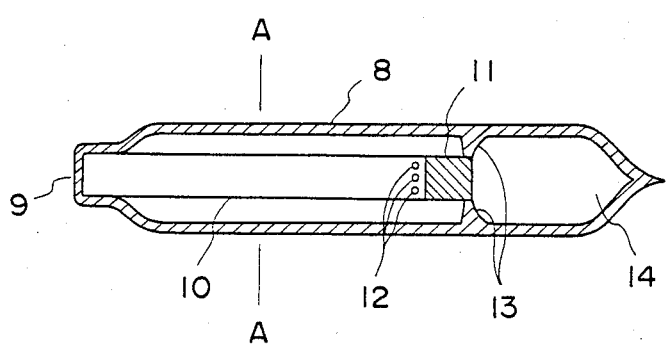
FIG. 4a is a longitudinal sectional view of a sampler according to one embodiment of this invention.
Figure 4B:
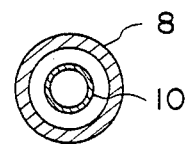

Referring first to FIGS. 4a and 4b of the drawings, a sampler according to this invention comprises a vacuum tubular body having a wall 8 formed from an inorganic refractory material of low thermal conductivity and substantially impermeable to hydrogen, and a sample-forming tube 10 supported by a holding members 13 extending inwardly from wall 8 in the tubular body and formed from a dehydrogenated thin steel sheet. The wall 8 is reduced in thickness at one end of the tubular body to define a readily meltable suction end 9. If the suction end 9 is immersed in molten metal, it is melted to form an opening, and molten metal is drawn into the tube 10. The tube 10 has a plurality of vent holes 12 and a dehydrogenated chiller metal or heat sink 11. The vent holes provide an opening to the inside of tube 10 to evacuate it before body 8 is closed at space 14. The holes 12 are small enough to prevent flow of the metal therethrough, as the metal is cooling. They also allow escape of any gas remaining in tube 10 as molten metal flows in so as to permit tube 10 to fill readily. Hydrogen is released from the molten metal in the tube 10 due to a reduction in its solubility as the molten metal is solidified due to loss of heat to the heat sink 11 and the remainder of the structure and radiation and is cooled. The hydrogen flows through the vent holes 12 or diffuses radially outwardly through the tube 10 into a hollow space 14 within the tubular body through the spaces between holding members 13 on the inside of wall 8.

Figure 5A:
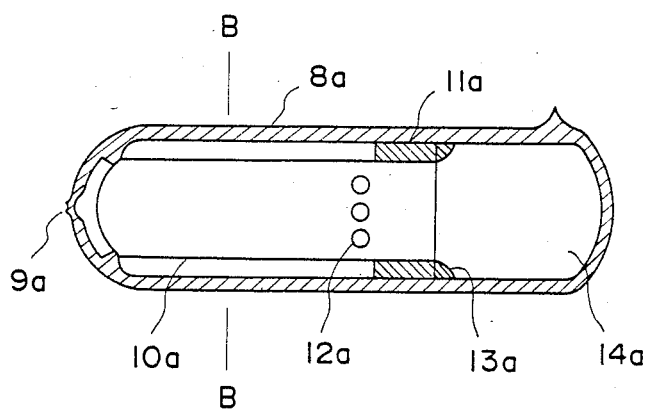
FIG. 5a is a longitudinal sectional view of a sampler according to another embodiment of this invention.
Figure 5B:
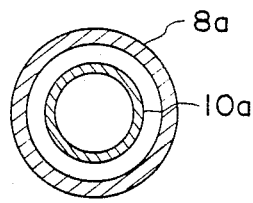

Another sampler according to this invention is shown in FIGS. 5a and 5b. It likewise comprises a tubular body having a wall 8a and a tube 10a formed from a thin steel sheet, but tube 10a is closed at the end adjacent suction end 9a and open into space 14a, and a sample of molten metal is drawn past projections 8b supporting the closed end of tube 10a into annular tubular space 8c defined between the wall 8a and the tube 10a. The reduced thickness suction end is shown at 9a, a chiller metal or heat sink at 11a for cooling the molten metal, vent holes at 12a to permit a vacuum to be drawn on space 8c before body 8a is closed at space 14a, yet small enough to prevent flow of the metal therethrough as the metal is cooling, and a holding member at 13a. As in the embodiment of FIGS. 4a–4c, the vent holes 12a also permit escape of any gas in space 8c as molten metal flows in so as to permit space 8c to fill readily. Hydrogen is similarly collected in a hollow space 14a. Hydrogen is released radially inwardly according to the sampler of FIGS. 5a and 5b, while being released radially outwardly in the sampler of FIGS. 4a and 4b.

Figure 6:
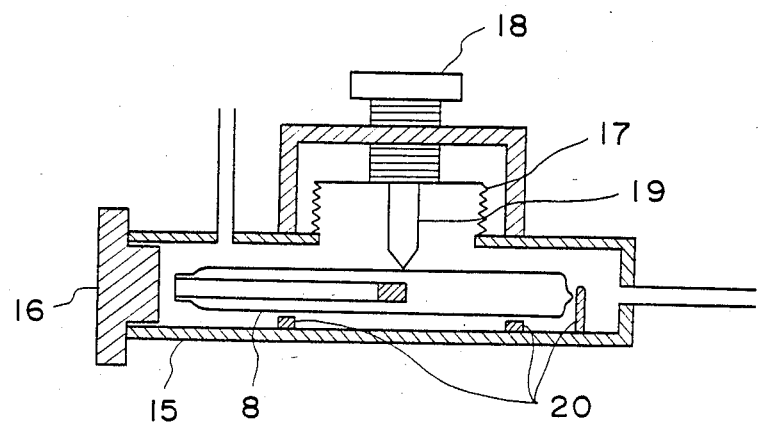
FIGS. 6 and 7 illustrate hydrogen collecting vessels embodying this invention.
Figure 7:
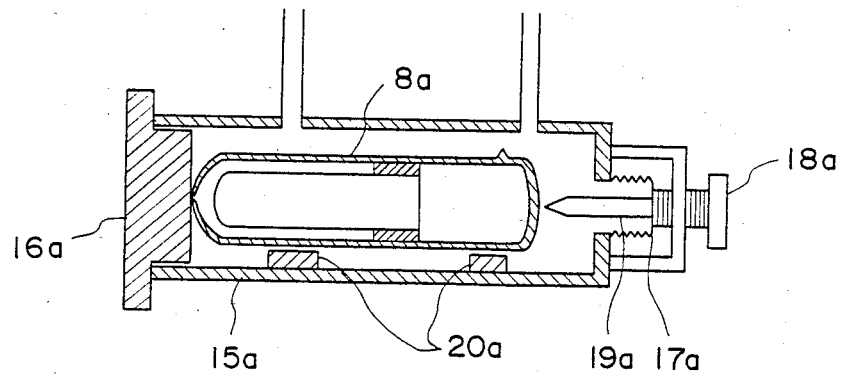

Referring to FIG. 6, there is shown by way of example a vessel 15 for collecting hydrogen from the sampler of FIGS. 4a and 4b, while FIG. 7 shows by way of example a vessel 15a for collecting hydrogen from the sampler of FIGS. 5a and 5b. Referring to FIG. 6, the sampler is completely inserted in the vessel 15 and the vessel 15 is closed by a cap 16. The vessel 15 is purged with a carrier gas, or evacuated, if required. A screw 18 is turned to compress the stainless steel bellows 17 welded to the vessel 15 and press a cutter 19 against the sampler supported on a plurality of supporting members 20 to cut an opening in the wall 8 so that hydrogen will be released from the sampler into the vessel 15. The vessel 15a of FIG. 7 is similarly used. The wall 8a of the sampler is cut by a cutter 19a to release hydrogen into the vessel 15a. The released hydrogen and the hydrogen released from the sample with the passage of time are delivered through a valve opening at regular intervals of time for direct determination by a mass spectrometer, or transported by a carrier gas for determination by a gas chromatograph and a thermal conductivity cell. In FIG. 7, a cap for the vessel 15a is shown at 16a, steel bellows at 17a, a screw at 18a and supporting members at 20a.

The wall 8 or 8a of the sampler is formed from an inorganic refractory material such as quartz or alumina, and is sufficiently resistant to heat not to melt when a sample is taken, and is gastight, except for the suction end 9 or 9a which is easily melted by the heat of the molten metal. It is preferable that a mold release agent, such as BN or graphite, be applied to the outer surface of the sampler to avoid the adhesion of molten metal or slag thereto. The inner tube 10 or 10a has been described as being made of a thin steel sheet, but may alternatively be formed from another metal such as aluminum or copper, or a gas-permeable refractory material such as a porous ceramic material or rockwool. In either event, it is important for the tube to be of such construction that a sample of molten metal is directly drawn into the tube 10 or around tube 10a through the suction end 9 or 9a. It is also important to heat the interior of the sampler and the inner tube at a high temperature in a vacuum for dehydrogenation and dehydration in order to ensure a reduction in blank test values. It is usually preferable that the hollow space in the sampler have a volumetric ratio of more than 1 to the metal sample therein, but even a ratio of less than 1 is effective if the molten metal has a small hydrogen content. A ratio not higher than 0.1 should, however, be avoided. It is possible to promote the release of hydrogen from the sample by heating it to a temperature not exceeding 150° C., as it is known that such heating does not appreciably affect the results of analysis.

The apparatus of this invention overcomes all of the drawbacks of the prior art sampler disclosed in Japanese Patent Publication No. 45157/1978, as will hereinafter be set forth.

(1) The sampler made of an inorganic refractory material, such as quartz or alumina, has a greatly improved resistance to the heat of molten metal, as compared with the prior art sampler. This is due not only to a difference in melting point, but also to a difference in thermal conductivity. Therefore, the sampler of this invention does not require any heat insulation, as opposed to the prior art sampler for which heat insulation has been essential. As there is no contamination of molten metal by any heat-insulating material, the sampler of this invention can be used for taking a sample of molten metal from a tundish or a continuous casting mold.

Figure 1:
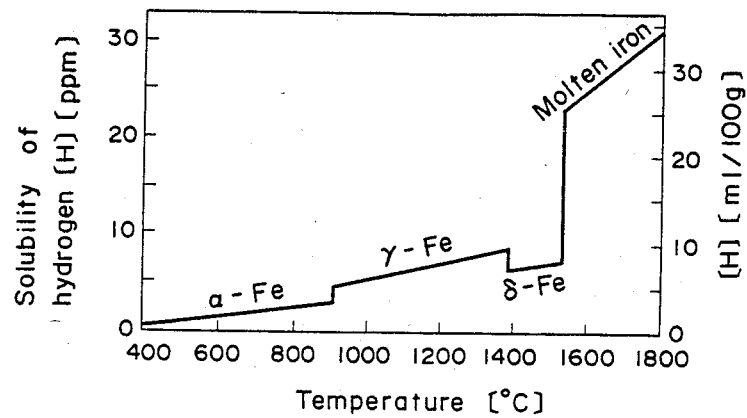
FIG. 1 is a graph showing the solubility of hydrogen under 1 atm. pressure of hydrogen in pure iron in relation to the temperture of the iron.
Figure 2:
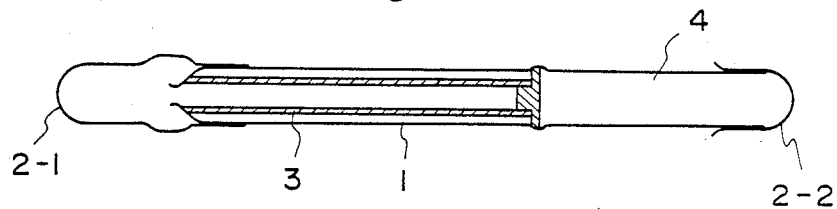
FIG. 2 illustrates a conventional sampler.
Figure 3:
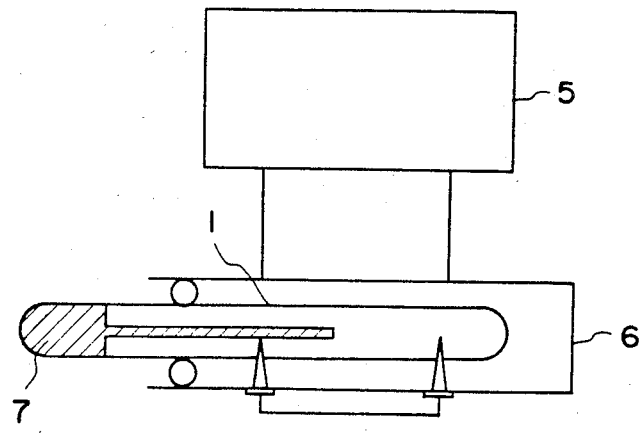
FIG. 3 schematically illustrates a gas analyzer for determining the hydrogen collected in the sampler of FIG. 2.

(2) The sampler of this invention does not have any melting cap of the type shown at 2 in FIG. 2 and has no end portion of the type shown at 7 in FIG. 3 and hereinbefore described as being likely to cause an analytical error. Therefore, the sampler can be completely inserted in the vessel 15 or 15a, and does not necessitate the use of any O-ring as hitherto required for achieving a seal between the sampler and the hydrogen collecting vessel. The sampler can be placed in the vessel 15 or 15a directly without being water cooled, since a metal packing member withstanding a high temperature can be used to provide a seal between the vessel 15 or 15a and its cap 16 or 16a. The elimination of water cooling enables a drastic increase in the percentage of the hydrogen which is released from the metal sample into the hollow space in the sampler. More specifically, the percentage is increased from about 90% to about 97%, and the amount of the hydrogen remaining in the solidified metal is almost negligible and does not make any appreciable difference from one sample to another. It is, therefore, possible to omit the determination of the remaining hydrogen and thereby shorten the analyzing time considerably.

(3) The suction end portion 7 of the prior art sampler has such a large a volume that a chiller metal is usually required for controlling appropriately the rate at which the molten metal in the end portion 7 is solidified. The presence of the chiller metal is another source of trouble. If, for example, the chiller cools the molten metal to a temperature of about 1500° C., the molten metal does not reach the inner tube or mold, but is solidified in the end portion, resulting often in the failure to obtain a satisfactory sample of molten metal. The sampler of this invention does not have any such intermediate end portion or any chiller therein, and therefore, can very satisfactorily form a sample even from molten metal having a temperature of, say, 1500° C.

The invention and its advantages will now be described more specifically with reference to a number of examples illustrating the hydrogen analysis of molten metal by the apparatus of this invention.

EXAMPLE 1

Figure 8:
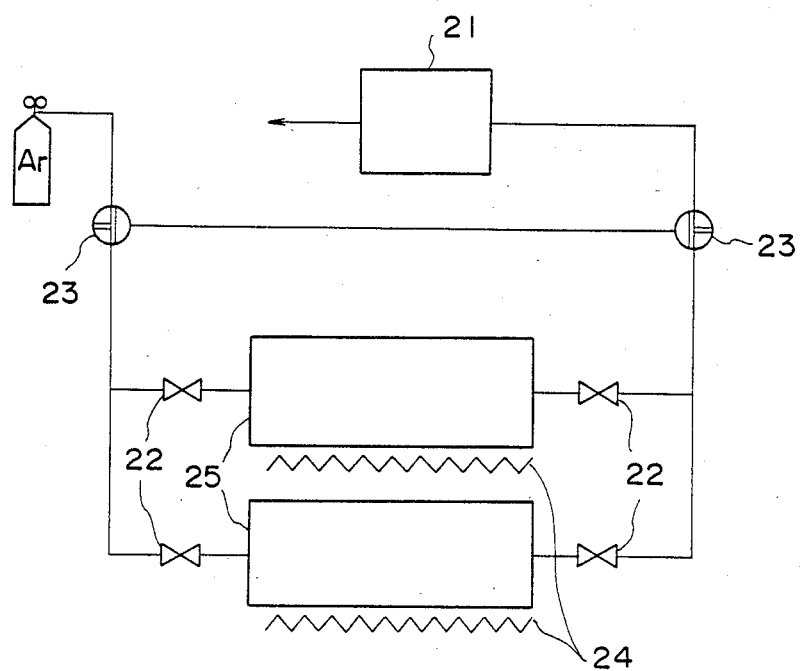
FIG. 8 diagrammatically illustrates an apparatus for hydrogen analysis embodying this invention.

Two samples were taken from molten steel in a continuous casting mold. The steel was of the composition designated by JIS (Japanese Industrial Standard) as SM50. A sampler of the construction shown in FIGS. 4a and 4b was used for taking the samples. The sampler had an outer wall of quartz having an outer diameter of 12 mm, an inside diameter of 10 mm and a length of 150 mm, and an inner tube formed from a dehydrogenated thin cold rolled steel sheet and having a wall thickness of 0.3 mm, a diameter of 6 mm and a length of 70 mm. The sampler had its interior evacuated to a pressure not exceeding $10^{-2}$ Torr. Each sample was placed in a stainless steel hydrogen collecting vessel directly without being cooled. Each vessel was of the construction shown in FIG. 6, and is shown at 25 in FIG. 8. The two vessels 25 were connected to a gas chromatograph-thermal conductivity detecting gas analyzer 21 as shown in FIG. 8. After the vessels 25 had been purged with argon gas, all valves 22 were closed, and the samplers were broken by the arrangement hereinbefore described with reference to FIG. 6. The valves 22 and three-way valves 23 were, then, opened to transport hydrogen by an argon carrier from each vessel 25 to a gas chromatograph for analysis by thermal conductivity determination. After the determination of the amount of hydrogen, each sampler was taken out and weighed, and the weight of the chiller and the inner tube was deducted from the weight of the sampler to obtain the weight of the sample. The hydrogen content of the molten metal was calculated from the quantity of the hydrogen released and the weight of the sample. Each sample was cut for the determination of the residual hydrogen by a method including melting in an inert gas, gas chromatography and thermal conductivity determination. For comparison purposes, two samples were taken from the same molten steel by a conventional pipette-aspirated quartz sampler. Each sample was cooled with water, cut, polished, weighed and subjected to the analysis of hydrogen by the method including melting in an inert gas, gas chromatography and thermal conductivity determination. The results are shown in TABLE 1.

TABLE 1

| | Hydrogen analysis (ppm) | | |
|---|---|---|---|
| | Total | Breakdown | |
| | hydrogen content a + b | a. Hydrogen released from the sample | b. Residual hydrogen |
| Invention | 2.71 | 2.61 | 0.10 |
| | 2.63 | 2.54 | 0.09 |
| Conventional | 1.70 | | |
| | 1.42 | | |

TABLE 1 shows the considerably worse results for the analysis made by the conventional apparatus. They are due to the loss of the hydrogen released from the molten metal during its solidification (a part of the quantity "a" in TABLE 1), the loss of a part of the hydrogen remaining in the sample ("b" in TABLE 1) during its cutting and polishing. These factors can greatly vary, and render the conventional apparatus unsatisfactory in the reproducibility of proper analysis. On the other hand, the apparatus of this invention ensures the analysis of hydrogen with a far higher degree of accuracy and reproducibility, since the problems of the prior art are basically overcome by a number of features including the inner tube construction and arrangement eliminating the undesirable end portion, the confinement of the entire sampler in the hydrogen collecting vessel, and the valves provided at the inlet and outlet of the vessel for enabling the determination of hydrogen released with the passage of time.

EXAMPLE 2

Two samples were taken from molten steel in a continuous casting mold. The steel was of the composition designated by JIS as SS41. A sampler of the construction shown in FIGS. 4a and 4b was used for taking the samples. The sampler had an outer wall of quartz having an outside diameter of 12 mm, an inside diameter of 10 mm and a length of 150 mm, and an inner tube formed from a dehydrogenated thin cold rolled steel sheet and having a wall thickness of 0.3 mm, a diameter of 6 mm and a length of 70 mm. The sampler had its interior evacuated to a pressure not exceeding $10^{-2}$ Torr. A mold release agent consisting of a fine powder of BN was sprayed in aerosol form onto the sampler. Each sample was placed directly, without being cooled, in a stainless steel hydrogen collecting vessel 25 (FIG. 8) which had been heated to 700° C. by a heater 24. The two vessels 25 were connected to a gas chromatograph-thermal conductivity detecting type gas analyzer 21 as shown in FIG. 8. After the vessels 25 had been purged with argon gas, all valves 22 were closed, and the samplers were broken. The valves 22 and three-way valves 23 were, then, opened to enable transportation of hydrogen by an argon carrier from each vessel 25 to the gas chromatograph 21 for analysis by thermal conductivity determination. A sample of molten steel was also taken by another sampler of the same construction. The weight of the sample was calculated from the difference between the vacant sampler weight and the weight of the sampler containing the sample, and the quantity of hydrogen per unit weight of the sample was thereby obtained. For comparison purposes, two samples were taken from the same molten steel by a conventional pipette-aspirated quartz sampler. Each sample was immediately cooled with water, cut, polished, weighed and subjected to the analysis for hydrogen by the method including melting in an inert gas, gas chromatography and thermal conductivity determination. The results are shown in TABLE 2.

TABLE 2

| | Hydrogen analysis (ppm) | |
| --- | --- | --- |
| | Hydrogen content as determined | Range |
| Invention | 3.71 | 0.05 |
| | 3.66 | |
| Conventional | 2.91 | 0.24 |

TABLE 2-continued

| Hydrogen analysis (ppm) | |
| --- | --- |
| Hydrogen content as determined | Range |
| 2.67 | |

TABLE 2 shows the considerably worse results for the analysis made by the conventional apparatus. They are apparently due to the loss of the hydrogen released from the molten steel during its solidification and the loss of hydrogen which takes place during the cutting and polishing of the sample. These factors can greatly vary, and render the conventional apparatus unsatisfactory in the reproducibility of proper analysis. The apparatus of this invention overcomes these problems, and enables a high degree of accuracy and reproducibility in hydrogen analysis.

Tests were conducted for ascertaining the effectiveness of a mold release agent for preventing the adhesion of molten steel or slag to the outer surface of the sampler. The tests were conducted on a plurality of quartz tubes having an outside diameter of 12 mm. Each of the tubes was closed at one end, BN or graphite in aerosol form was applied to its outer wall, and the tube was immersed in molten steel. The test results are shown in TABLE 3.

TABLE 3

| | Tests of the effectiveness of mold release agents | | | |
| --- | --- | --- | --- | --- |
| Mold release agent | Number of tubes tested | Number of tubes to which no molten steel or slag adhered | Number of tubes to which molten steel or slag adhered | Effectiveness (%) |
| BN | 20 | 20 | 0 | 100 |
| Graphite | 20 | 20 | 0 | 100 |
| None | 20 | 0 | 20 | 0 |

Although only BN and graphite have been mentioned, it is also possible to use any other mold release agent, such as SiC, TiC, TiN or $Al_2O_3$, if it can form a film which reduces the wetting property of the molten steel or slag and prevents its adhesion to the outer wall of the sampler, and if it is not a source of hydrogen. The agent does not necessarily need to be applied in aerosol form, but can also be applied by, for example, the coating of its solution in water or an organic solvent, or evaporation.

EXAMPLE 3

Blank tests were conducted on three samplers of the construction shown in FIGS. 4a and 4b. Each of the samplers had an outer wall of quartz and an inner tube which had been dehydrogenated by heating at 850° C. for an hour in a vacuum having a pressure of $1 \times 10^{-4}$ Torr. Prior to its closure, each sampler had its interior dehydrogenated and dehydrated by heating at 1000° C. for two hours in a vacuum having a pressure of $1 \times 10^{-4}$ Torr. Then, the sampler was heated under the conditions simulating those of sample heating, i.e., at 1000° C. for 30 minutes in the ambient air, and broken in the apparatus of FIG. 8, though it was not heated by the heater 24. The test results are shown in TABLE 4.

TABLE 4

Blank test results on three samplers

| Average (ppm)* | Difference (ppm)* |
|---|---|
| 0.11 | 0.03 |

*Based on an average sample weight of 5.2 g.

As is obvious from TABLE 4, the dehydrogenation and dehydration of a sampler prior to its closure are effective for maintaining low blank test values.

Samples were taken from non-deoxidized steel by the sampler of this invention and the conventional sampler disclosed as to Japanse Patent Publication No. 45157/1978, and the samplers were compared with each other in the filling ratio, i.e., the ratio of the theoretical weight of a completely filled sampler to the actual weight of a sampler filled with molten steel. The results are shown in TABLE 5.

TABLE 5

| | Filling ratio (%) | | | | | | | |
|---|---|---|---|---|---|---|---|---|
| | 1 | 2 | 3 | 4 | 5 | 6 | Average | Difference |
| Invention | 103.3 | 99.3 | 99.3 | 99.4 | 100.0 | 98.9 | 100.0 | 4.4 |
| Conventional | 80.0 | 66.2 | 89.9 | 86.0 | 84.7 | 92.7 | 86.6 | 32.6 |

As is obvious from TABLE 5, the sampler of this invention showed a filling ratio of nearly 100% without any bubbling despite the use of the steel which had not been deoxidized. There was no appreciable variation from one sample to another. On the other hand, the conventional sampler showed a considerably lower, largely variable ratio due to bubbling, and was found unsuitable for non-deoxidized steel. The formation of bubbles was apparently closely related to a sharply drop in sampling efficiency resulting from a slight drop in molten steel temperature, and due to the cooling of the molten steel by the chiller in the suction end portion of the sampler and the generation of CO resulting from a reduction in its solubility in the steel.

Samples of deoxidized steel were taken by the sampler of this invention which had been closed after degassing by heating and coated with BN as a mold release agent, and by the conventional sampler disclosed in the Japanese Patent Publication mentioned above. They were broken and analyzed by the apparatus of FIG. 8 or 3, as the case may be. The results are shown in TABLE 6. As is obvious from TABLE 6, the values obtained by the conventional sampler were smaller and varied over a wider range than those obtained by the sampler of this invention. This was apparently due to the likelihood of bubbles being formed in the conventional sampler and trapping hydrogen, and the loss of a part of the residual hydrogen which apparently occurred when the inner mold was cut for residual hydrogen analysis.

TABLE 6

| | Hydrogen analysis (ppm) | | | |
|---|---|---|---|---|
| | Invention | Conventional | | |
| | Hydrogen released from sample | Hydrogen released from sample | Residual hydrogen | Total |
| 1 | 4.31 | 3.85 | 0.33 | 4.18 |
| 2 | 4.68 | 4.08 | 0.33 | 4.41 |
| 3 | 4.19 | 3.32 | 0.38 | 3.70 |
| 4 | 4.31 | 3.26 | 0.33 | 3.59 |
| 5 | 4.27 | 3.95 | 0.33 | 4.28 |
| 6 | 4.49 | 3.65 | 0.33 | 3.98 |
| 7 | 3.92 | 3.97 | 0.33 | 4.29 |
| 8 | 4.21 | 3.33 | 0.35 | 3.68 |
| 9 | 4.57 | 3.54 | 0.29 | 3.83 |
| 10 | 4.15 | 4.13 | 0.33 | 4.46 |
| 11 | 4.40 | 2.58 | 0.32 | 2.90 |
| 12 | 4.61 | 2.71 | 0.33 | 3.04 |
| X | 4.34 | 3.53 | 0.332 | 3.86 |
| R | 0.76 | 1.55 | 0.09 | 1.56 |

What is claimed is:

1. A sampler for drawing a sample of molten metal for analysis for hydrogen, said sampler comprising:
   a tubular body of inorganic refractory material having low thermal conductivity and being substantially impermeable to hydrogen, and having a readily meltable portion at one end and a hydrogen collection chamber at the other end;
   an inner tube completely enclosed within said tubular body and being of a hydrogen permeable metal impermeable material capable of withstanding the temperature of the molten metal being sampled and having a cylindrical space therewithin and means for mounting said inner tube within said tubular body for defining with the inner surface of said tubular body an annular space between said inner tube and said body, said inner tube having apertures therein communicating said spaces, one of said spaces being open at the end corresponding to said one end of said tubular body to said readily meltable portion for receiving molten metal thereinto when the meltable portion is melted when the one end of the sampler is inserted into a bath of molten metal; and
   means sealing the end of said one space which is toward the other end of said tubular body from said hydrogen collection chamber, the other of said spaces being open to the hydrogen collection chamber at the end corresponding to the other end of said tubular body, and having the end corresponding to the one end of said tubular body closed off from said readily meltable portion.

2. A sampler as claimed in claim 1 in which said means for sealing said one space from said hydrogen collection chamber is a metal heat sink.

3. A sampler as claimed in claim 1 in which said one space is said cylindrical space and said other space is said annular space.

4. A sampler as claimed in claim 1 in which said one space is said annular space and said other space is said cylindrical space.

5. A sampler as claimed in claim 1 in which at least a portion of the outer peripheral surface of said tubular body which is brought into contact with the molten metal being sampled is coated with a mold release agent.

6. A sampler as claimed in claim 1 in which said inorganic refractory material is taken from the group consisting of quartz and alumina.

7. An apparatus for analyzing the hydrogen content of molten metal, comprising:
   a sampler for drawing a sample of molten metal, said sampler being constituted by:

a tubular body of inorganic refractory material having low thermal conductivity and being subtantially impermeable to hydrogen, and having a readily meltable portion at one end and a hydrogen collection chamber at the other end;

an inner tube completely enclosed within said tubular body and being of a hydrogen permeable metal impermeable material capable of withstanding the temperature of the molten metal being sampled and having a cylindrical space therewithin and means for mounting said inner tube within said tubular body for defining with the inner surface of said tubular body an annular space between said inner tube and said body, said inner tube having apertures therein communicating said spaces, one of said spaces being open at the end corresponding to said one end of said tubular body to said readily meltable portion for receiving molten metal thereinto when the meltable portion is melted when the one end of the sampler is inserted into a bath of molten metal;

means sealing the end of said one space which is toward the other end of said tubular body from said hydrogen collection chamber, the other of said spaces being open to the hydrogen collection chamber at the end corresponding to the other end of said tubular body, and having the end corresponding to the one end of said tubular body closed off from said readily meltable portion;

a hermetically closed vessel for holding said sampler containing a sample;

means for forming part of said vessel for breaking said sampler while it is hermetically sealed in said vessel; and gas analyzer means connected to said vessel for determining the quantity of hydrogen released from said sampler into said vessel when said sampler is broken. /

* * * * *